United States Patent
Schuette et al.

(10) Patent No.: US 6,544,621 B1
(45) Date of Patent: Apr. 8, 2003

(54) FLOOR COVERING ARTICLES COMPRISING ANTIMICROBIAL ADHESIVE LATEX COMPONENTS

(75) Inventors: Robert L. Schuette, Boiling Springs, SC (US); John G. Lever, Spartanburg, SC (US); N. David Sellman, Jr., LaGrange, GA (US)

(73) Assignee: Milliken & Company, Spartanburg, SC (US)

( * ) Notice: Subject to any disclaimer, the term of this patent is extended or adjusted under 35 U.S.C. 154(b) by 337 days.

(21) Appl. No.: 09/654,491

(22) Filed: Sep. 1, 2000

(51) Int. Cl.7 .................................. B32B 33/00
(52) U.S. Cl. ................. 428/97; 428/95; 428/96
(58) Field of Search .................. 428/95, 97, 96; 424/78.1, 618

(56) References Cited

U.S. PATENT DOCUMENTS

| | | | | |
|---|---|---|---|---|
| 4,911,898 A | * | 3/1990 | Hagiwara et al. | 423/700 |
| 5,736,591 A | | 4/1998 | Dunn | 523/122 |
| 6,013,275 A | * | 1/2000 | Konagaya et al. | 424/443 |
| 6,306,371 B1 | * | 10/2001 | Wong et al. | 424/49 |
| 6,342,212 B1 | * | 1/2002 | Schuette et al. | 424/618 |
| 6,455,610 B1 | * | 9/2002 | Lever et al. | 523/122 |

FOREIGN PATENT DOCUMENTS

| KR | 2002001896 A | * | 1/2002 | C08J/5/00 |
|---|---|---|---|---|

* cited by examiner

*Primary Examiner*—Cheryl A. Juska
(74) *Attorney, Agent, or Firm*—Terry T. Moyer; William S. Parks

(57) ABSTRACT

Floor covering products, such as carpets, carpet tiles, floor mats, and the like, which comprise very specific antimicrobial adhesive latex formulations therein are provided. Such formulations comprise, as the only antimicrobial active ingredients, certain inorganic antimicrobial compounds, such as, preferably, silver-containing ion-exchange, glass, and/or zeolite compounds. Such latexes exhibit excellent adhesive and antimicrobial qualities and, since they do not contain any added organic bactericides (and thus no bactericide VOCs), do not release any such organic bactericides upon exposure to high processing temperatures.

4 Claims, No Drawings

# FLOOR COVERING ARTICLES COMPRISING ANTIMICROBIAL ADHESIVE LATEX COMPONENTS

FIELD OF THE INVENTION

This invention relates to floor covering products, such as carpets, carpet tiles, floor mats, and the like, which comprise very specific antimicrobial adhesive latex formulations therein. Such formulations comprise, as the only antimicrobial active ingredients, certain inorganic antimicrobial compounds, such as, preferably, silver-containing ion-exchange, glass, and/or zeolite compounds. Such latexes exhibit excellent adhesive and antimicrobial qualities and, since they do not contain any added organic bactericides (and thus no bactericide VOCs), do not release any such organic bactericides upon exposure to high processing temperatures.

DISCUSSION OF THE PRIOR ART

All U.S. Patents listed below are herein entirely incorporated by reference.

There has been a great deal of attention in recent years given to the hazards of bacterial contamination from potential everyday exposure. Noteworthy examples of such concern include the fatal consequences of food poisoning due to certain strains of *Eschericia coli* being found within undercooked beef in fast food restaurants; Salmonella contamination causing sicknesses from undercooked and unwashed poultry food products; and illnesses and skin infections attributed to *Staphylococcus aureus, Klebsiella pneumoniae,* yeast, and other unicellular organisms. With such an increased consumer interest in this area, manufacturers have begun introducing antimicrobial agents within various household products and articles. For instance, certain brands of polypropylene cutting boards, liquid soaps, etc., all contain antimicrobial compounds. The most popular antimicrobial for such articles is triclosan. Although the incorporation of such a compound within liquid or certain polymeric media has been relatively simple, other substrates, including the surfaces of textiles and fibers, have proven less accessible. Furthermore, triclosan includes chlorine ions which, upon dissociation, may release to the substrate surface. Such ions are potentially hazardous to humans, due to skin irritation upon contact, as well as within environmental effluents, and the like. Additionally, harmful microbes have shown, on occasion, an ability to develop an immunity to the bactericidal properties of triclosan. Also, surface treatments with triclosan have proven ineffective as well since such compounds are highly water soluble and are easily removed upon exposure to sufficient amounts of moisture. There thus remains a long-felt need to provide a short- and long-term effective, durable, and long-lasting antimicrobial agent for surface utilization within adhesive latex formulations. Of additional importance is the need to provide such formulations which, upon exposure to high temperature processing conditions (either in the production of or incorporation of such formulations within other applications, such as carpet backing, and the like) do not require the presence of organic bactericides which may result in the release of a certain volatile organic content (VOC) upon such high temperature processing.

One proposed latex has utilized metal ions for bactericidal properties, but also requires the presence of an organic bactericide to provide the desired level of antimicrobial activity. U.S. Pat. No. 5,736,591 to Dunn teaches the addition of certain metal ions, including copper, silver and any other Group Ib metals, as salts (such as silver nitrate, silver perchlorate, and the like) to latex formulations in combination with such organic compounds as 2-methyl-4, 5-trimethylene-4-isothiazolin-3-one, to provide a bactericidal latex. No mention is made anywhere within this patent of the availability, much less, the capability of silver-based ion-exchange or zeolite compounds as potential antimicrobial agents. Nor is there any discussion of the ability of any such silver-based compounds providing effective antimicrobial activity without the need for any added organic bactericides.

Such specific silver-containing inorganic microbiocides (e.g., ion-exchange and/or zeolite compounds) have recently been developed and utilized as antimicrobial agents on and within a plethora of different substrates and surfaces. In particular, such microbiocides have been adapted for incorporation within plastic compositions and fibers in order to provide household and consumer products which inherently exhibit antimicrobial characteristics. Although such silver-based agents provide excellent, durable, antimicrobial properties, to date no teachings exist which teach or fairly suggest the presence of such inorganic compounds within adhesive latex formulations. This is not surprising considering the difficulties which have been noted in attempting such an introduction of these large molecular weight, bulky, compounds within polymer latex formulations to begin with. For instance, such inorganic compounds may interfere with the desired adhesives qualities of the latex if and when such large molecules are present at the surface. One would anticipate that a large surface accumulation of such bulky compounds would reduce the potential surface-to-surface interaction required for the adhesive formulation to function properly. Furthermore, it has been found that the addition of such bulky compounds within already-compounded latex formulations is extremely difficult. The resultant composition generally exhibits discrete areas of concentrated, dark-colored, antimicrobial compound. Not only does this result in an unpleasing aesthetic appearance, but such a latex, being nonuniform in dispersion as well, may exhibit uneven adhesive properties, too. Although these problems exist, there is a desire to incorporate such silver-based inorganic antimicrobial agents within adhesive latex formulations in order to provide a regenerable, highly effective, long-lasting antimicrobial latex at, on, or within various different articles.

Of importance in this situation, such a novel adhesive latex permits an effective manner of providing a "cleaner" floor covering article. Generally, the main concern with such articles is the difficulty in effectively and throughly cleaning and/or disinfecting the area at or above which the face fibers are attached to the primary backing fabric. As most vacuum cleaners, steam cleaners, etc., do not reach to such an area, this portion of a floor covering article is generally the most susceptible to microbe accumulation and growth. Hence, the incorporation of an effective latex is necessary to provide microbe control in such inaccessible locations. In the past, antimicrobial latex formulations have been utilized for such a purpose. However, such as in U.S. Pat. No. 5,736,591, such formulations have required the presence of organic bactericides which exhibit problems during production. Most notably, the amount incorporated within such floor covering latexes is quite high due to the invariable loss of a substantial amount during high temperature processing during article production. Not only does this require greater cost to the consumer to account for this loss of bactericide, but this also results in the release of volatile organic compounds (VOCs) potentially into the atmosphere. Thus, there is a need to provide floor coverings comprising non-organic bactericide containing adhesive latex formulations which still provide effective adhesion and antimicrobial activity. Unfortunately, to date, no such floor covering article, or antimicrobial adhesive latex for that matter, has been accorded the carpet or floor mat industry by the pertinent prior art.

DESCRIPTION OF THE INVENTION

It is thus an object of the invention to provide a floor covering product which exhibits antimicrobial activity in the portion where the face fabric is attached to its primary backing fabric and which does not comprise any organic bactericides as VOCs. Another object of the invention is to provide an antimicrobial adhesive latex exhibiting a substantially uniform appearance and possessing no VOC content.

Accordingly, this invention encompasses a floor covering article comprising at least: a face fiber portion, a primary backing fabric portion, and a secondary backing portion; wherein said primary backing is integrally attached to said face fiber portion, and said secondary backing is adhered to said primary backing, wherein all of said face fiber portion, said primary backing fabric portion, and said secondary backing portion are in contact with an adhesive latex, wherein said adhesive latex formulation comprises at least one polymer constituent, at least one thickening agent (in order to provide a latex having a viscosity of, preferably, at least 4,000 cps at 25° C. and at 1 atmosphere), and at least one inorganic silver-based antimicrobial agent selected from the group consisting of silver-based ion-exchange compounds, silver-based zeolites, silver-based glasses, and any mixtures thereof, wherein said formulation does not include any added organic bactericide compounds The term floor covering, as noted above, is intended to cover any standard articles which comprise face fibers and which are utilized to cover surfaces on which people are prone to walk. Thus, carpets (broadloom, tile, or otherwise) and floor mats (outdoor, indoor, and the like) are the primary articles concerned within this invention. The term face fiber portion encompasses any standard fibers and composites thereof, which are utilized within floor coverings. As mere examples, nylon, polyethylene, polypropylene, cotton, polyvinylacetate, and the like, fibers may be tufted through a fabric (such as a woven, non-woven, or knit fabric of any fiber type, such as those listed previously), which happens to be what is intended to be encompassed by the term primary backing portion. Also, the face fiber portion may be monofilament, core-sheath fiber, and the like, or may be present as berber or any other type of carpet face.

Initially, prior to integration with any other components, the face fiber portion is sewn, tufted, needled, and the like, through the primary backing fabric to form a composite which can then be simply adhered to a further portion. Alternatively, the primary backing fabric may be contacted with the secondary backing fabric and the face fiber portion may then be created by the needling, etc., through the primary backing fabric. Basically, any number of alternatives are available for production of the inventive floor covering product. Examples of carpet and carpet tile production are disclosed within U.S. Pat. No. 5,929,145 to Higgins et al., U.S. Pat. No. 5,948,500 to Higgins et al., U.S. Pat. No. 5,545,276 to Higgins et al., and U.S. Pat. No. 5,540,968 to Higgins et al. Examples of floor mat production are present within U.S. Pat. No. 5,902,662 to Kerr, U.S. Pat. No. 5,928,446 to Kerr et al., and U.S. Pat. No. 5,305,565 to Nagahama et al.

The term secondary backing portion is intended to be rather broad since the important issue with regard to such a component is the contact with the inventive latex between that layer and the primary backing fabric. Such a secondary layer then may be of any standard carpet or floor mat backing, or intermediate layer. Thus, if it is a carpet, the secondary backing may be a polyolefin fabric, or a polyurethane foam (for cushioning purposes) or simply a fabric layer to which a polyurethane foam is attached. If it is a floor mat, the secondary backing may be a sheet of solid or foamed rubber most likely, although, again, such a backing may be an intermediate layer of fabric, rubber, and the like, between the primary backing fabric and an outer layer.

The term adhesive latex is intended to encompass any thickened formulation of already-made polymer constituents which possesses a viscosity of at least viscosity of, preferably, at least 125,000 cps at 25° C. and at 1 atmosphere and which also exhibits an affinity for different surfaces which results in the ability to create a stationary interaction between the latex and the target surface without the needed presence of any other adhesive initiators, additives, compounds, or other compositions. Such latices are well known throughout the pertinent art (such as within U.S. Pat. No. 5,736,591) and may be utilized within any variety of applications which require extremely thick adhesives, including, without limitation, carpet backings, sealant compositions (for ceramic tiles, for example), and the like. The term polymer constituent is intended to encompass any polymeric material capable of being in latex form. Such constituents thus include, without limitation, olefins, acrylics, urethanes, vinylidene chlorides, vinyl acetates, vinyl pyridines, aromatics, silicones, and any copolymers thereof. Most preferably, the latex is a styrene butadiene rubber (SBR) latex, a polyurethane latex, a polyvinylidene chloride latex, a carboxylated SBR latex, and the like. Such polymer constituents within this invention include, without limitation, and preferably, HPL 8455NA (a vinylidene chloride) from Dow, and R101 (SBR rubber) from Reichold. The amount of polymer constituent present within the inventive latex ranges from about 10 to about 65% by weight of the total composition. Preferably, this amount is from about 20 to about 60%; more preferably from about 25 to about 50%; most preferably from about 30 to about 50%.

Such latices are preferably of high solids content to provide high adhesive properties. As such, the latex should be, as noted above, of rather high viscosity in order to stabilize the solid compounds in composition. Such a viscosity, as measured at 25° C. and at 1 atmosphere pressure, is at least 125,000 cps; preferably between about 150,000 and 1,000,000 cps; more preferably from about 200,000 cps to about 900,000 cps; and most preferably from about 250,000 cps to about 750,000 cps. The necessary thickener added to the polymer constituent is thus of prime importance. A thickener such as an alginate, methylcellulose, carboxylmethylcellulose, hydroxyethylcellulose, carboxylmethylcellulose, hydroxypropylcellulose, a gum, such as gum arabic, guar gum, and any combinations thereof, and the like, are preferred, although any standard thickening agent may be utilized. The amount of thickener is highly dependent on the desired target viscosity. Generally, then, the amount should be from about 0.005 to about 5% by weight of the total latex formulation; preferably from about 0.01 to about 3%; more preferably from about 0.015 to about 1%; and most preferably from about 0.02 to about 0.5%.

The term inorganic silver-based antimicrobial material is intended to encompass any such silver-containing solid compound which is primarily inorganic in nature (some organic component is permitted, although the primary antimicrobial portion must be inorganic), is a solid at standard temperature and pressure, and which exhibits antimicrobial activity. Preferably, such material is a silver-based ion-exchange compound, a silver-based zeolite, or a silver-based glass, and any combinations thereof. The preferred silver-based ion exchange material is an antimicrobial silver zirconium phosphate available from Milliken & Company, under the tradename ALPHASAN®. Other potentially preferred silver-containing solid inorganic antimicrobials in this invention is a silver-substituted zeolite available from Sinanen under the tradename ZEOMIC® AJ, or a silver-substituted glass available from Ishizuka Glass under the tradename IONPURE®, may be utilized either in addition to or as a substitute for the preferred species. Other possible compounds, again without limitation, are silver-based materials such as AMP® T558 and MICROFREE®, both available from DuPont, as well as JMAC®, available from Johnson Matheny. Generally, such a metal compound is added in an amount of from about 0.00001 to 10% by total weight of the particular latex composition; preferably from about 0.001 to about 5%; more preferably from about 0.01 to about 1%; and most preferably from about 0.1 to about 1.0%.

Other possible components within the inventive latex composition include water, (as a diluent), fillers, such as calcium carbonate (to provide strength and hardness to the latex, as well as to fill any "empty spaces" for a uniform strength dispersion), flame retardants, such as antimony oxide, available from Great Lakes Chemical, emulsifiers and/or surfactants (to provide more effective interaction with target surfaces and/or to provide foaming for easier application to target surfaces). Of these components, the fillers are generally added in large amounts within such latex formulations for the strength and hardness purposes.

As noted above, such an inventive comprises no organic bactericide compounds and thus does not include any appreciable VOC content. This is of vital importance to ensure that utilization of such a latex does not result in the release of environmentally and/or physically hazardous organics, particularly upon exposure to high temperatures (e.g., above about 100° C.). The inventive adhesive latex is preferably compounded with all of the required components simultaneously added together in order to provide the most uniform product, from both appearance and physical performance perspectives. Thus, simultaneous compounding of the polymer constituent, thickener, and silver-based inorganic antimicrobial agent are required (as well as the other potential additives) for this purpose. Adding such solid antimicrobial agents after compounding is extremely difficult without the production of highly undesirable discolorations (e.g., darkening, particularly if high temperatures are utilized for further processing).

The particular silver-based inorganic antimicrobial agent should exhibit an acceptable log kill rate after 24 hours in accordance with the AATCC Test Method 100-1983. Such an acceptable level log kill rate is tested for *Staphylococcus aureus* or *Klebsiella pneumoniae* of at least 0.1 increase over baseline. Alternatively, an acceptable level will exist if the log kill rate is greater than the log kill rate for non-treated (i.e., no solid inorganic antimicrobial added) latices (such as about 0.5 log kill rate increase over control, antimicrobial-free latices). Preferably these log kill rate baseline increases are at least 0.3 and 0.3, respectively for *S. aureus* and *K pneumoniae;* more preferably these log kill rates are 0.5 and 0.5, respectively; and most preferably these are 1.0 and 1.0, respectively. Of course, the high end of such log kill rates are much higher than the baseline, on the magnitude of 5.0 (99.999% kill rate). Any rate in between is thus, of course, acceptable as well. However, log kill rates which are negative in number are also acceptable for this invention as long as such measurements are better than that recorded for correlated non-treated latices. In such an instance, the antimicrobial material present within the latex at least exhibits a hindrance to microbe growth.

The preferred embodiments of these alternatives fabric treatments are discussed in greater detail below.

DESCRIPTION OF THE PREFERRED EMBODIMENTS

Examples of particularly preferred compounds within the scope of the present invention are set forth below.

Adhesive Latex Production

The preferred inventive adhesive latices were compounded in accordance with the Table below with all of the components admixed together. The resultant viscosity of each of these compositions are listed as ranges.

Adhesive Latex Formulations

EXAMPLE 1

SBR Latex Production

| Component | Amount added (in weight by pounds) |
|---|---|
| R101 | 27,254 |
| Water | 1,857 |
| Calcium Carbonate | 14,444 |
| Anionic Surfactant | 360 (froth aid) |
| Antimicrobial | (as listed below) |
| Sodium polyacrylate | 1,100 |
| Chemwet 1396-A | 141 (penetrant surfactant) |

The resultant compounded formulation exhibited a viscosity of approximately 5,500 cps.

EXAMPLE 2

Vinylidene Chloride Latex Production

| Component | Amount added (in weight by pounds) |
|---|---|
| HPL 8455NA | 24,154 |
| Water | 1,900 |
| Calcium Carbonate | 15,983 |
| Anionic Surfactant | 495 (froth aid) |
| Antimicrobial | (as listed below) |
| Sodium polyacrylate | 1,045 |

The resultant compounded formulation exhibited a viscosity of approximately 5,500 cps.

The Antimicrobial material tested was ALPHASAN® RC 5000 and RC 7000 and, for comparison purposes, Durotex 5000 (an isothiazoline-based bactericide from Rohm and Haas). The resultant latices were then utilized as carpet backing components during the production of carpet tiles which involved combining at least three carpet components together, namely the face fibers (e.g., pile fibers), the primary backing fabric (through which the face fiber is introduced), and the secondary backing fabric or a polyurethane foam backing or an olefinic-based resin backing. The adhesive latex was introduced, initially as a puddle, to the side of the primary backing fabric prior to contacting with the secondary backing. The puddle was then spread over the primary backing fabric surface and pressed therein. Subsequently, the secondary backing, in this case a polyurethane foam, was pressed to the adhesive surface. Upon heating, the entire composite remained together very strongly as desired.

The face fibers were then coated and immersed into separation preparations of microbes, namely, *S. aureus* and *K. pneumoniae*. After an exposure of 24 hours, the carpet was then tested for log kill rates of such microbes in accordance with AATCC Test Method 100–1993. The results for each of the formulations noted above, in combination with the specific antimicrobial agents as noted above, are in tabular form below:

| EXPERIMENTAL DATA TABLE Log Kill Rates for *S. aureus* and *K. pneumoniae* | | |
|---|---|---|
| Latex Composition # | Antimicrobial Type (% by weight) | Log Kill Rate for *S. aureus* |
| 1 | ALPHASAN ® RC 5000 (0.12%) | 1.05 |
| 1 | ALPHASAN ® RC 5000 (0.25%) | 0.62 |
| 1 | ALPHASAN ® RC 7000 (0.12%) | 1.80 |
| 1 | ALPHASAN ® RC 7000 (0.25%) | 2.30 |
| 2 | ALPHASAN ® RC 5000 (0.33%) | 1.44 |
| 2 | ALPHASAN ® RC 5000 (0.66%) | 1.52 |
| 2 | ALPHASAN ® RC 7000 (0.33%) | 0.77 |
| 2 | ALPHASAN ® RC 7000 (0.66%) | 0.90 |
| | (Comparative Examples) | |
| 1 | Durotex 5000 (0.20%) | 0.28 |
| 1 | Durotex 5000 (0.40%) | 0.30 |
| 2 | Durotex 5000 (0.33%) | 0.10 |
| 2 | Durotex 5000 (0.66%) | 0.20 |

Thus, the inventive adhesive latex exhibits excellent adhesive and antimicrobial properties.

There are, of course, many alternative embodiments and modifications of the present invention which are intended to be included within the spirit and scope of the following claims.

What we claim is:

1. A floor covering article comprising at least: a face fiber portion, a primary backing fabric portion, and a secondary backing portion; wherein said primary backing is integrally attached to said face fiber portion, and said secondary backing is adhered to said primary backing, wherein all of said face fiber portion, said primary backing fabric portion, and said secondary backing portion are in contact with an adhesive latex, wherein said adhesive latex formulation comprises at least one polymer constituent, at least one thickening agent, and at least one inorganic silver-based antimicrobial agent selected from the group consisting of silver-based ion-exchange compounds, silver-based zeolites, silver-based glasses, and any mixtures thereof, wherein said formulation does not include any added organic bactericide compound.

2. The floor covering article of claim 1 wherein said at least one silver-based antimicrobial agent is a silver-based ion-exchange compound.

3. The floor covering article of claim 1 wherein said article is a carpet.

4. The floor covering article of claim 2 wherein said article is a carpet.

* * * * *